(12) United States Patent
Chan

(10) Patent No.: US 10,391,121 B2
(45) Date of Patent: Aug. 27, 2019

(54) MAGNESIUM CHLORIDE COMPOSITION FOR DERMATOLOGICAL USE

(71) Applicant: BioPharmX, Inc., Menlo Park, CA (US)

(72) Inventor: Kin F. Chan, Los Gatos, CA (US)

(73) Assignee: BioPharmX, Inc., San Jose, CA (US)

( * ) Notice: Subject to any disclaimer, the term of this patent is extended or adjusted under 35 U.S.C. 154(b) by 0 days.

(21) Appl. No.: 15/970,683

(22) Filed: May 3, 2018

(65) Prior Publication Data

US 2018/0318342 A1 Nov. 8, 2018

Related U.S. Application Data

(60) Provisional application No. 62/501,078, filed on May 3, 2017.

(51) Int. Cl.
| | | |
|---|---|---|
| *A61K 33/06* | (2006.01) | |
| *A61P 17/10* | (2006.01) | |
| *A61K 9/00* | (2006.01) | |
| *A61K 47/10* | (2017.01) | |
| *A61K 47/38* | (2006.01) | |
| *A61K 47/02* | (2006.01) | |
| *A61K 47/44* | (2017.01) | |
| *A61K 47/08* | (2006.01) | |

(52) U.S. Cl.
CPC ............ *A61K 33/06* (2013.01); *A61K 9/0014* (2013.01); *A61K 47/02* (2013.01); *A61K 47/10* (2013.01); *A61K 47/38* (2013.01); *A61P 17/10* (2018.01); *A61K 47/08* (2013.01); *A61K 47/44* (2013.01)

(58) Field of Classification Search
None
See application file for complete search history.

(56) References Cited

U.S. PATENT DOCUMENTS

| 4,154,816 | A | * | 5/1979 | Roehl | ................... A61K 8/0229 424/65 |
|---|---|---|---|---|---|
| 4,518,582 | A | | 5/1985 | Schamper et al. | |
| 4,725,430 | A | * | 2/1988 | Schamper | ............ A61K 8/0229 424/66 |
| 5,567,426 | A | * | 10/1996 | Nadaud | ................... A61K 8/042 424/401 |
| 5,851,556 | A | | 12/1998 | Breton et al. | |
| 5,898,037 | A | * | 4/1999 | Marx | ..................... A61Q 19/08 424/49 |
| 7,258,875 | B2 | | 8/2007 | Chiou | |
| 7,704,518 | B2 | * | 4/2010 | Tamarkin | ............... A61K 8/046 424/405 |
| 2011/0223222 | A1 | * | 9/2011 | Spyros Botsaris | ...... A61K 8/34 424/401 |
| 2015/0125496 | A1 | * | 5/2015 | Yamamoto | ........... A61K 9/0014 424/400 |
| 2016/0279152 | A1 | | 9/2016 | Chen et al. | |

FOREIGN PATENT DOCUMENTS

WO WO 2018/204711 A1 11/2018

OTHER PUBLICATIONS

International Search Report and Written Opinion from International Application No. PCT/US2018/030976, 7 pages, dated Jul. 24, 2018, application now published as International Publication No. WO2018/204711 on Nov. 8, 2018.

\* cited by examiner

*Primary Examiner* — Jennifer A Berrios
(74) *Attorney, Agent, or Firm* — McDermott Will & Emery LLP; Judy M. Mohr; Wen Li

(57) ABSTRACT

Provided herein is a topical composition and related methods for making and using the composition. In a first aspect, the topical composition comprises a magnesium salt (e.g. magnesium chloride) dissolved in an anhydrous or non-aqueous solvent. Exemplary solvents comprise a monohydric aliphatic alcohol, and a polyol.

19 Claims, No Drawings

MAGNESIUM CHLORIDE COMPOSITION FOR DERMATOLOGICAL USE

CROSS-REFERENCE TO RELATED APPLICATIONS

This application claims the benefit of U.S. Provisional Application No. 62/501,078, filed May 3, 2017, incorporated herein by reference in its entirety.

TECHNICAL FIELD

This disclosure relates generally to compositions and methods for preparing such compositions, as well as to related uses. Uses include, for example, the treatment of various dermatological conditions and diseases, among other things. More particularly, this disclosure is directed to compositions comprising a magnesium salt, a monohydric aliphatic alcohol, and a polyol, and to related methods for making and using such compositions.

BACKGROUND

Epsom salts (magnesium sulfate) have been used to treat a variety of skin conditions when mixed with water. There is a need for a topically-applied composition that delivers magnesium chloride to the skin in quantities sufficient to inhibit growth of *Propionibacterium acnes* (*P. acnes*) bacteria on the skin surface and to actively draw water out of the skin.

BRIEF SUMMARY

The present disclosure overcomes one or more limitations associated with current magnesium-salt containing topical compositions. Provided herein is a topical composition comprising a magnesium salt (e.g. magnesium chloride or magnesium sulfate) and a non-aqueous solvent system comprised of a monohydric aliphatic alcohol and a polyol, wherein the composition does not comprise a tetracycline-class drug, and wherein the monohydric aliphatic alcohol and polyol comprise 30-99.9% of the weight of the composition. In some related embodiments, the ratio of monohydric aliphatic alcohol to polyol is in a range of 1:1 to 99:1 by weight.

In yet one or more further embodiments, the composition comprises a greater percent by weight of the monohydric aliphatic alcohol than the polyol. For example, in one or more related embodiments, the w/w ratio of monohydric aliphatic alcohol to polyol is in a range of about 2:1 to 10:1 by weight.

In yet one or more further embodiments, the magnesium salt is dissolved in the non-aqueous solvent. In other embodiments, the magnesium salt is dissolved in the composition. In another embodiment, the magnesium salt is dissolved in the composition upon its application to skin and subsequent to its application on skin. In another embodiment, the magnesium salt is dissolved in the composition upon its application to skin, whereupon the monohydric aliphatic alcohol evaporates from the composition to form a residual composition, and the magnesium salt is dissolved in the residual composition.

In some further embodiments, the monohydric aliphatic alcohol is selected from the group consisting of ethanol, isopropanol, propyl alcohol, tert-butyl alcohol, or combinations thereof. In some particular embodiments, the monohydric aliphatic alcohol is ethanol.

In yet some additional embodiments, the topical composition comprises from about 0.1% to about 10% by weight magnesium chloride.

In yet some additional embodiments, the topical composition comprises from about 0.5% to about 2% by weight magnesium chloride.

In yet some additional embodiments, the topical composition comprises about 1.2% by weight magnesium chloride.

In yet one or more further embodiments, the polyol is a C3-C8 diol or a triol. In some embodiments, the polyol is propylene glycol.

In some further embodiments, the topical composition comprises from about 0.005% to about 3.0% by weight of a sulfite compound. In one or more particular embodiments, the sulfite is selected from the group consisting of sodium sulfite, sodium bisulfite, and sodium meta-bisulfite.

In yet some additional embodiments, the topical composition comprises less than about 3 weight percent water. In yet some further embodiments, the topical composition comprises less than about 2 weight percent water.

In some further embodiments, the topical composition further comprises an essential oil. In one or more related embodiments, the essential oil is 1,8-cineole. In some embodiments, the topical composition comprises from about 0.01 to 5 weight percent of 1,8-cineole.

In some further embodiments, the topical composition comprises a thickening agent. In one or more related embodiments, the thickening agent is hydroxypropyl cellulose.

In some further embodiments, the topical composition has an effective pH of 3.5-8.0 when mixed with water in a ratio of 1:9 by weight. In some embodiments, the topical composition has an effective pH of about 5.0 to about 7.5 when mixed with water in a ratio of 1:9 by weight.

In yet one or more additional embodiments, the composition is non-irritating when applied to rats daily over a period of 28 days. For instance, a non-irritating composition will generally not irritate the skin or cause an allergic reaction.

In one or more embodiments of the composition, the monohydric aliphatic alcohol is a liquid at room temperature. In one or more further embodiments, the monohydric aliphatic alcohol is selected from the group consisting of ethanol, isopropanol, propyl alcohol, tert-butyl alcohol, and combinations thereof.

In yet some further embodiments, the monohydric aliphatic alcohol is a volatile monohydric aliphatic alcohol.

In yet some additional embodiments related to the polyol component, the polyol is a liquid at room temperature. In one or more particular embodiments, the polyol is a C3-C8 diol or triol. In yet some more particular embodiments, the polyol is propylene glycol.

In yet some additional embodiments directed to the polyol, the polyol is not glycerol or glycerin.

In some particular embodiments of the composition, the magnesium salt is selected from the group consisting of magnesium chloride, magnesium sulfate, magnesium salicylate, and combinations thereof.

In some particular embodiments of the composition, the magnesium salt is selected from the group consisting of anhydrous magnesium chloride, anhydrous magnesium sulfate, anhydrous magnesium salicylate, and combinations thereof.

In one or more further embodiments, the composition further comprises a thickening agent. In some particular embodiments, the thickening agent is hydroxypropyl cellulose.

In some further embodiments of the composition, the composition possesses a viscosity in a range of about 75 centipoise to about 10,000 centipoise at 25° C. In some further embodiments of the second aspect, the composition comprises one or more additional additives, such as, for example, an antioxidant, a thickener, a colorant, or other suitable additive.

In some further embodiments, the topical composition is not an emulsion.

In some further embodiments, the composition is not an emulsion and/or does not comprise nanoparticles or microparticles.

In some further embodiments, the composition does not comprise an antibiotic. In some further embodiments, the composition does not comprise a tetracycline-class drug. In some further embodiments, the composition does not comprise minocycline.

In some further embodiments, the composition does not comprise a retinoid.

In some further embodiments, the composition does not comprise an active pharmaceutical ingredient (API).

In some further embodiments, the composition does not comprise added water. In one embodiment, the composition does not comprise exogenous or exogenously added water.

In some further embodiments, the composition does not comprise polyethylene glycol.

In some further embodiments, the composition does not comprise an oil.

In some further embodiments, the composition does not comprise an oil other than 1,8-cineole.

In some further embodiments, the composition does not comprise more than 5% of a calcium salt by weight. In some further embodiments, the composition does not comprise more than 1% of a calcium salt by weight. In some further embodiments, the composition does not comprise a calcium salt. In some further embodiments, the composition does not comprise calcium.

In some further embodiments, the composition is not occlusive.

In some additional embodiments, the topical composition does not comprise nanoparticles or microparticles.

In certain embodiments, the topical composition is non-aqueous. In alternative embodiments, the topical composition is anhydrous. In certain embodiments, the composition comprises less than 10% water as measured by Karl Fisher. In certain embodiments, the composition comprises less than 5% water as measured by Karl Fisher. In certain embodiments, the composition comprises less than 2% water as measured by Karl Fisher.

In some embodiments, the concentration of the magnesium chloride in the topical composition exceeds the minimum inhibitory concentration (MIC) of magnesium chloride for a target bacteria in a target tissue or target body fluid. In one or more related embodiments, the target bacteria is *P. acnes*.

In yet some further embodiments, the composition dries in less than 60 seconds when applied to a region of skin in vivo.

In yet some additional embodiments in which the composition comprises a polyol and 1,8-cineole, the combination of the polyol and the 1,8-cineole is effective to prevent the skin from scaling and from extreme drying due to extended use for two weeks or more when applied at least 3 times per week.

Also provided herein is a method of treating acne in a human subject comprising topically applying an effective amount of a composition as provided herein to an exterior epithelial body surface of the human. In one embodiment, the composition is topically applied to an affected area of the epithelial body surface.

Also provided herein is a method of treating rosacea in a human subject comprising topically applying an effective amount of a composition as provided herein to an exterior epithelial body surface of the human. In one embodiment, the composition is topically applied to an affected area of the epithelial body surface.

In yet a further aspect, provided is a method for treating a condition or disease responsive to treatment with magnesium chloride in a human, where the method comprises topically applying a composition as provided herein to an exterior epithelial surface of a human body at least daily for a period of at least 1 week. In one or more related embodiments, the condition or disease is a dermatological condition or disease, and the applying step comprises applying the topical composition to the skin once or twice daily for a period of from about 6 to about 52 weeks.

In one or more additional embodiments, the dermatological condition or disease is acne or rosacea. In one or more particular embodiments, the acne is acne vulgaris. In yet or more alternative embodiments, the acne is acne fulminans.

In another aspect, a method for treating a subject having acne is provided. The method comprises topically applying a composition as described herein to a local skin region affected by acne. The method is effective to reduce the inflammatory lesion count by at least 25% or at least 50% when applied daily for a period of from about 6 to about 52 weeks. In one or more embodiments, the method is effective to result in at least a 2-point reduction in acne intensity score according to the Investigator's Global Assessment (IGA) scale ("Guidance for Industry: Acne Vulgaris: Developing Drugs for Treatment", U.S. Department of Health and Human Services, Food and Drug Administration, September 2005) when the composition is topically applied daily for 6-52 weeks to a human with an initial acne intensity score of in the range of 3 to 4, or in the range of 2 to 4.

In one embodiment, the Investigator's Global Assessment (IGA) for acne or rosacea for the human subject is reduced from moderate or severe to clear or almost clear following 12 weeks of daily application of the topical formulation.

In another embodiment, the acne lesion count or rosacea lesion count for the human subject reduced by more than 10 lesions following 12 weeks of daily application of the topical formulation.

In another aspect, a method for improving or alleviating a symptom associated with a dermatological disease or condition is provided. The method comprises topically applying a composition as described herein to a local skin region presenting a symptom of the disease or condition. In one embodiment, the composition is applied to an external skin surface from one to three times daily for a period of from about 2 weeks to at least about 6 weeks or until a visible improvement in the symptom of the dermatological condition or disease is observed.

In yet one or more further embodiments, provided is a composition as described herein accompanied by instructions for topical use for treatment of a dermatological condition or disease of the skin. In one or more related embodiments, the instructions comprise instructions for applying the composition to an external skin surface from one to three times daily for a period of from about 2 weeks to at least about 6 weeks or until a visible improvement in the dermatological condition or disease is observed.

In yet an additional aspect, provided herein is a method for making a composition, e.g., one suitable for treating acne or rosacea in a human, preferably a topical composition, the method comprising (i) combining a magnesium salt, a volatile monohydric aliphatic alcohol, and a polyol to form a mixture, and (ii) agitating the mixture from (i) to form a solution in which the magnesium salt is dissolved.

In yet another aspect, provided is a method for making a composition, the method comprising (i) combining a magnesium salt and a non-aqueous solvent to form a mixture, and (ii) agitating the mixture from (i) to form a solution in which the magnesium salt is dissolved.

Each of the foregoing aspects and embodiments is meant to apply to each and every other aspect and embodiment. Additional embodiments of the composition, related methods, components of the composition, and the like will be apparent from the following description, examples and claims. These and other objects and features of the disclosure will become more fully apparent when read in conjunction with the following detailed description.

DETAILED DESCRIPTION

The present invention will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As can be appreciated from the foregoing and following description, each and every feature described herein, and each and every combination of two or more of such features, is included within the scope of the present disclosure provided that the features included in that such combinations are not inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

All publications, patents and patent applications cited herein are hereby incorporated by reference in their entirety, unless otherwise indicated. In an instance in which the same term is defined both in a publication, patent, or patent application incorporated herein by reference and in the present disclosure, the definition in the present disclosure represents the controlling definition. For publications, patents, and patent applications referenced for their description of a particular type of compound, chemistry, etc., portions pertaining to such compounds, chemistry, etc. are those portions of the document that are incorporated herein by reference.

Definitions

It must be noted that, as used in this specification, the singular forms "a," "an," and "the" include plural referents unless the context clearly dictates otherwise. Thus, for example, reference to an "active ingredient" includes a single ingredient as well as two or more different ingredients, reference to a "solvent" refers to a single solvent as well as to two or more different solvents or a complex mixture of solvents, reference to a "magnesium salt" includes a single magnesium salt as well as two or more different magnesium salts, and the like.

In describing and claiming the present invention, the following terminology will be used in accordance with the definitions described below.

The term "topical composition" refers to a material that comprises pharmaceutically acceptable ingredients, including an active ingredient, and is intended for administration to an animal or human subject and is applied to the surface of the skin, in contrast to materials that are taken orally or via intravenous (subdermal) injection. A topical composition is generally intended to have its intended effect at the site of application and does not result in significant concentrations of active ingredient in the bloodstream or other tissues (as is the case with, for example, transdermal compositions). Topical compositions as provided herein are typically administered for the purpose of alleviation of symptoms associated with a dermatological disease or condition, treatment of a dermatological disease or condition, or prevention of a dermatological disease or condition.

The term "solvent" refers to a substance in which one or more solid ingredients are dissolved to some extent. For example, ethanol, isopropanol, and propylene glycol, to name a few, are considered as solvents for magnesium chloride and other magnesium salts.

The term "tetracycline-class drug" refers to tetracycline and tetracycline derivatives such as, for example, minocycline, doxycycline, oxytetracycline, and their corresponding pharmaceutically acceptable salt forms, as well as solvates and hydrates thereof, including various crystalline forms, polymorphs, amorphous materials, etc. A tetracycline antibiotic generally contains a four ring octahydrotetracene-2-carboxamide skeleton, while the actual substituents on the skeleton may vary.

The term "monohydric aliphatic alcohol" refers to a monofunctional organic compound that contains a single hydroxyl group, in which the hydroxyl functional group is covalently attached to a saturated carbon atom forming part of a branched or linear alkyl chain, and which does not contain an aromatic-ring configuration of atoms. Generally, a monohydric aliphatic alcohol for use in the compositions provided herein conforms to the formula R—OH, where R is a $C_1$-$C_4$ alkyl. Suitable R groups include ethyl, propyl, isopropyl, butyl, sec-butyl, isobutyl and tert-butyl.

The term "polyol" refers to a pharmaceutically acceptable alcohol containing two or more hydroxyl groups, and possessing from 3-8 carbon atoms. Polyols suitable for use in the instant compositions may but do not necessarily contain functional groups in addition to the hydroxyl groups, such as e.g., an ether bond. As used herein, polyethylene glycol shall not be considered to be a polyol. Illustrative polyols include diols such as propylene glycol (PG) and dipropylene glycol, triols such as glycerol, 1,2,6 hexanetriol, trimethylolpropane, and higher alcohols (i.e., containing more than 3 hydroxyl groups) such as sorbitol and pentaerythritol. Polyols also include butylene glycol, hexylene glycol, 1,6 hexanediol, mannitol, and xylitol. It is recognized that some of these solvents are solids that may be undesirable, but when combined in appropriate mixtures, they may be suitable for use in a topical composition as described herein.

The term "cineole" refers to 1,8-cineole.

The term "cosmetic" refers to an item that is an "article intended to be rubbed, poured, sprinkled, or sprayed on, introduced into, or otherwise applied to the human body for cleansing, beautifying, promoting attractiveness, or altering the appearance" (from U.S. FD&C Act, section 201(i)). The U.S. Food and Drug Administration classifies various items as cosmetics or drugs. This definition is intended to follow the U.S. FDA classifications. U.S. FDA further clarifies on its web site that "Among the products included in this definition are skin moisturizers, perfumes, lipsticks, fingernail polishes, eye and facial makeup preparations, cleansing shampoos, permanent waves, hair colors, and deodorants, as well as any substance intended for use as a component of a cosmetic product."

The term "topical", in reference to administration of an active ingredient or composition, refers to application of such active ingredient or composition to an exterior epithelial surface of the body, including the skin or cornea. For purposes of this application, applications inside a bodily orifice, such as the mouth, nose, or ear shall not be considered to be topical applications.

A solvent (or solvents) is said to "dissolve" a magnesium salt (or conversely, the salt is said to be soluble in a solvent) if the solubility of that salt at 25° C. is at least 0.1% (w/w). For emulsions and the like, the salt is only considered to "dissolve" in the solvent if the salt is in direct interaction with the solvent such that the salt is incorporated into the solvent to form a solution. So, for example, a salt that is coated to limit interaction with a solvent would not be considered dissolved in that solvent if it remained in particulate form. A salt may separate into ionic components with solvent dissolving the ionic components. In such cases, the solvent is said to dissolve the salt.

A solvent or composition is said to be "anhydrous" or to have "no added water" if there is no added water in the solvent or composition. That is to say, as used herein, an anhydrous composition is one in which water has not been added as a component. For clarity, a solution or composition can be considered to be anhydrous even if it contains water arising from a composition component, such as through the addition of magnesium chloride hexahydrate, as long as no free water is added to the composition. Many of the solvents described herein are hydroscopic to a greater or lesser extent and such solvents may be part of an anhydrous composition without regards to the water that is naturally absorbed by such materials.

A solvent or composition is said to be "non-aqueous" if there is less than 5% by weight water content in the solvent or composition, respectively, as measured by Karl Fischer titration or other suitable method.

A solvent or composition is said to be "volatile" if it has a boiling point of less than 100° C. at atmospheric pressure. Volatile solvents or compositions typically evaporate readily at room temperature and atmospheric pressure. Examples of volatile solvents include isopropanol, ethanol, and t-butyl alcohol. Examples of non-volatile solvents include water, white petrolatum, and olive oil.

"Room temperature" refers to a temperature in a range of about 20-25 degrees Centigrade (20-25° C.). In reference to a measurement or other feature requiring a precise indication of room temperature, room temperature is taken as 25 degrees centigrade.

"MIC" or minimum inhibitory concentration is defined as the lowest concentration of an antimicrobial compound that will inhibit the visible growth of a microorganism after 48 hours of incubation.

The abbreviation "(w/w)" indicates that relative concentrations of components in a composition are presented on a "weight for weight" basis (i.e. percentages refer to a percentage of the total weight), rather than on the basis of volume or some other basis.

The term "viscosity" refers to the measurement of a substance using a viscometer, such as a Brookfield LVF viscometer (Brookfield Engineering Laboratories, Inc., Middleboro, Mass.) or equivalent, with spindle and speed combinations suitable for the testing of applicable viscosity level.

As used herein, "dermatological condition" refers to cosmetic and pathological disorders of the skin. Dermatological conditions include topical inflammatory skin conditions such as eczema, seborrhoeic dermatitis, bullous dermatoses, cutaneous sarcoidosis, Kaposi's sarcoma, neutrophilic dermatoses, contact dermatitis, rosacea, psoriasis and acne including acne rosacea, and infections such as Impetigo, cellulitis, erysipelas, folliculitis, furuncles, carbuncles, Lyme disease, and other skin infections.

As used herein, "acne" is a disorder of the skin characterized by papules, pustules, cysts, nodules, comedones, and other blemishes or skin lesions. These blemishes and lesions are often accompanied by inflammation of the skin glands and pilosebaceous follicles, as well as, microbial, especially bacterial, infection. As used herein, acne includes all known types of acne. Some types of acne include, for example, acne vulgaris, cystic acne, acne atrophica, bromide acne, chlorine acne, acne conglobata, acne cosmetica, acne detergicans, epidemic acne, acne estivalis, acne fulminans, halogen acne, acne indurata, iodide acne, acne keloid, acne mechanica, acne papulosa, pomade acne, premenstral acne, acne pustulosa, acne scorbutica, acne scrofulosorum, acne urticata, acne varioliformis, acne venenata, propionic acne, acne excoriee, gram negative acne, steroid acne, nodulocystic acne and acne rosacea. Acne rosacea is characterized by inflammatory lesions (erythema) and telangiectasia. Telangiectasia is abnormally and permanently dilated blood vessels associated with a number of diseases. For example, facial telangiectasia is associated with age, acne rosacea, sun exposure, and alcohol use.

The term "pharmaceutically acceptable" in reference to an entity or ingredient is one that may be included in the compositions provided herein and that causes no significant adverse toxicological effects in the patient at specified levels, or if levels are not specified, in levels known to be acceptable by those skilled in the art. All ingredients in the compositions described herein are provided at levels that are pharmaceutically acceptable. For clarity, active ingredients may cause one or more side effects and inclusion of the ingredients with a side effect profile that is acceptable from a regulatory perspective for such ingredients will be deemed to be "pharmaceutically acceptable" levels of those ingredients.

"Pharmaceutically acceptable salt" denotes a salt form of a drug or active ingredient having at least one group suitable for salt formation that causes no significant adverse toxicological effects to the patient. Reference to an active ingredient as provided herein is meant to encompass its pharmaceutically acceptable salts. Pharmaceutically acceptable salts include salts prepared by reaction with an inorganic acid, an organic acid, a basic amino acid, or an acidic amino acid, depending upon the nature of the functional group(s) in the drug. Suitable pharmaceutically acceptable salts include acid addition salts which may, for example, be formed by mixing a solution of a basic drug with a solution of an acid capable of forming a pharmaceutically acceptable salt form of the basic drug, such as hydrochloric acid, iodic acid, fumaric acid, maleic acid, succinic acid, acetic acid, citric acid, tartaric acid, carbonic acid, phosphoric acid, sulfuric acid and the like. Typical anions for basic drugs, when in protonated form, include chloride, sulfate, bromide, mesylate, maleate, citrate, phosphate, and the like. Suitable pharmaceutically acceptable salt forms and methods for identifying such salts are found in, e.g., Handbook of Pharmaceutical Salts: Properties, Selection and Use, Weinheim/Zürich:Wiley-VCH/VHCA, 2008; P. H. Stahl and C. G. Wermuth, Eds.

"Non-irritating" in reference to a topical formulation as provided herein refers to a formulation having an average score of less than 0.50 on the modified Draize scale for a test of 5 or more Sprague-Dawley rats. The modified Draize test is an acute irritation test carried out as follows. A Sprague-Dawley rat is shaved in an application area, and the application area allowed to rest for approximately 24 hours and then rinsed with non-irritating soap. A test composition is applied evenly, without significant rubbing, to a 10 cm$^2$ area of the rat's skin in a volume of 2.5 mg/cm$^2$. The sample is allowed to sit uncovered for 24 hours. After 24 hours, the application area is washed gently with 1× phosphate buffered saline (1×PBS) and non-irritating soap to facilitate observation of the application area. The application area is then scored according to the following scale: 0=no evidence of irritation; 1=minimal erythema, barely perceptible; 2=definite erythema, readily visible, minimal edema or minimal popular response; 3=erythema and papules; 4=definite edema; 5=erythema, edema, and papules; 6=vesicular eruption; 7=strong reaction spreading beyond test site.

"Therapeutically effective amount" is used herein to mean the amount of a preparation, or amount of an active ingredient in the preparation, that is needed to provide a desired level of active ingredient in a target tissue or at a target site. The precise amount will depend upon numerous factors, e.g., the particular active ingredient, the components and physical characteristics of the preparation, intended patient population, patient considerations, and the like, and can readily be determined by one skilled in the art, based upon the information provided herein and available in the relevant literature.

The term "patient" refers to a living organism suffering from or prone to a condition that can be prevented or treated by administration of a composition as provided herein, and includes both humans and animals. Preferred animals are mammals.

"Optional" or "optionally" means that the subsequently described circumstance may or may not occur, so that the description includes instances where the circumstance occurs and instances where it does not.

In many cases, the patent application describes ranges of values. Such ranges shall be construed to include the endpoints of the range unless doing so would be inconsistent with the text or otherwise noted.

Topical Composition

In a first aspect, a composition that treats certain dermatological conditions is provided. The composition comprises a magnesium salt (e.g. magnesium chloride or magnesium sulfate) and a non-aqueous solvent comprising a monohydric aliphatic alcohol and a polyol. The composition does not comprise a tetracycline-class drug, in one embodiment. In another embodiment, the monohydric aliphatic alcohol and polyol comprise 50-99.9% of the weight of the composition. In one embodiment, magnesium chloride is a preferred magnesium salt due to its low skin irritation and its low skin toxicity.

Anhydrous or non-aqueous compositions and solvents (e.g. anhydrous or non-aqueous monohydric aliphatic alcohol) are desirable because it is beneficial for the magnesium salt to dehydrate the skin surface. Dehydrating the skin surface limits the water that is available to bacteria on the skin surface which reduces the survival rate for potentially harmful or detrimental bacteria. Use of anhydrous or non-aqueous compositions and solvents thus promotes the reduction of the bacterial concentration on the skin surface and supports the treatment or prophylaxis of dermatological conditions and diseases. Furthermore, using anhydrous forms of magnesium salts, rather than their hydrates (e.g. magnesium chloride anhydrous instead of magnesium chloride hexahydrate) further promotes these beneficial effects by allowing the magnesium salts to attract water and thus promote the drying of the skin surface.

The present application provides a topical composition and related methods for preparing the topical composition. In one aspect, the topical composition comprises a magnesium salt in a non-aqueous solvent, where details regarding the magnesium salt and the non-aqueous solvent are provided above and in the sections which follow.

In another aspect, provided herein is a topical composition comprising a magnesium salt, a monohydric aliphatic alcohol, and a polyol, wherein the magnesium salt is dissolved within the topical composition. In some exemplary embodiments, the monohydric aliphatic alcohol is ethanol, isopropanol, or tert-butyl alcohol (i.e., t-butyl alcohol). In one or more additional exemplary embodiments, the polyol is a C3-C8 aliphatic, saturated diol or triol. In one or more further embodiments, the polyol is a 1,2-diol, a 1,3-diol or a triol. Illustrative polyols include propylene glycol, dipropylene glycol, and glycerol. Further details of the composition and related methods are provided herein.

Materials can be sourced, for example, from the following providers: ethanol (anhydrous) (Spectrum Chemicals, Gardena, Calif.), propylene glycol (Spectrum Chemicals, Gardena, Calif.), 1,8-cineole (Penta International Company, Livingston, N.J.), hydroxypropyl cellulose (Ashland, Inc., Covington, Ky.), sodium meta-bisulfate (Spectrum Chemicals, Gardena, Calif.), and magnesium chloride (anhydrous) (Sigma-Aldrich Corp., St. Louis, Mo.).

In some embodiments, the composition is used for the treatment of a dermatological condition or disease. Non-limiting examples of dermatological conditions or diseases for which the composition may be used include but are not limited to acne, rosacea, seborrhoeic dermatitis, psoriasis, and superficial skin infections such as impetigo, as well as in wound management.

Accordingly, in one aspect, the topical composition comprises a magnesium salt in a non-aqueous or anhydrous solvent. In another aspect, the composition comprises a magnesium salt, a monohydric aliphatic alcohol, and a polyol. Composition components and features will now be described in greater detail.

The amount of magnesium salt in the topical composition (e.g., magnesium chloride or magnesium sulfate) typically ranges from about 0.01% to about 10% by weight, or from about 0.1% to about 5% by weight. In one embodiment, the magnesium salt is present in the composition from about 0.1% to about 4% by weight, or from about 0.2% to about 3% by weight or from about 0.2% to about 1.5% by weight. In another embodiment, the topical formulation may comprise any one of the following weight percentages of magnesium salt: 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 1.0%, 2.1%, 2.2%, 2.3%, 2.4%, 2.5% and so forth.

Illustrative magnesium salts include but are not limited to magnesium bromide, magnesium chloride, magnesium fluoride, magnesium iodide, magnesium sulfate, magnesium salicylate, and magnesium phosphate. In preferred embodiments, the magnesium salt is anhydrous.

The topical composition generally additionally comprises, as part of its non-aqueous or anhydrous solvent system, a monohydric aliphatic alcohol, preferably a volatile alcohol. Generally, a monohydric aliphatic alcohol for use in the compositions provided herein conforms to the formula R—OH, where R is a $C_1$-$C_4$ alkyl group. Suitable R groups include methyl, ethyl, propyl, isopropyl, butyl, sec-butyl, isobutyl and tert-butyl. Preferably, the monohydric aliphatic alcohol is a primary alcohol such as ethyl alcohol, propyl alcohol or butyl alcohol. One particularly preferred monohydric aliphatic alcohol is ethanol. In some embodiments, the monohydric aliphatic alcohol is one having a solubility in water of 5 percent or greater at room temperature. Methanol, ethanol, 1- and 2-propanol, and t-butyl alcohol, for example, are miscible with water, while 1-butanol has a solubility of about 9% in water and 2-butaol has a solubility in water of 7.7% at room temperature. Preferred alcohols are hydrophilic.

Yet a further component of the topical composition (i.e., forming part of its solvent system) is a polyol containing two or more hydroxyl groups, and possessing from 3-8 carbon atoms. Typically, the polyol is an aliphatic compound; exemplary polyols for use in the instant composition include diols such as propylene glycol (PG, propane-1,2-diol), hexylene glycol (2-methylpentane-2,4-diol), 1,3-butylene glycol (1,3-butane diol), and dipropylene glycol, triols such as glycerol and trimethylolpropane, and higher alcohols (meaning containing more than 3 hydroxyl groups) such as sorbitol and pentaerythritol. Preferred polyols are C3-C8 diols and triols. The diol or triol will typically have a molecular weight less than about 250 Daltons, or even less than about 200 Daltons. In some instances, the polyol will have a molecular weight less than about 125 Daltons. The polyol, may, in some instances, be hygroscopic, such as in the case of propylene glycol. In some embodiments, the polyol is a triol other than glycerol or glycerin.

Many monohydric aliphatic alcohols, such as ethanol, can provide a stable solvent for magnesium salts. Since ethanol is a volatile solvent, much of the solvent evaporates quickly when applied to the skin where the surface temperature is typically between about 33.5-36.9° C. For example, in one embodiment, the solvent evaporates and/or penetrates into the skin when applied to the skin in less than about 3 minutes, 2 minutes, 1.5 minutes or 1 minute. This evaporation and/or penetration increase the concentration of the magnesium salt in the composition remaining on the surface of the skin and can lead to formation of solid deposits on the skin surface or in the upper layers of the skin. Formation of solid deposits is less favorable than maintaining the magnesium salt in solution because the dissolved form provides better chemical interaction between the magnesium salt and the skin bacteria and the water within the skin and at the skin surface. The compositions provided herein are aimed, at least in part, in overcoming the shortcomings noted above. For example, consider a composition comprising 1.2% (w/w) magnesium chloride, 78.8% (w/w) ethanol, and 20% (w/w) propylene glycol. The ethanol is more volatile than the propylene glycol, such that even if all of the ethanol evaporates from the skin and/or penetrates into the skin, the concentration of the magnesium chloride in the residual composition following evaporation of ethanol would be approximately 5.6%. Magnesium chloride is soluble at room temperature and/or at skin surface temperature in propylene glycol at levels above this concentration, which means that in the foregoing example, the magnesium chloride will desirably remain in solution (i.e., in a dissolved state), especially at the elevated temperature of the skin. Moreover, the concentration of magnesium chloride in the residual composition would be less than that described in this calculation, as some of the ethanol would transport magnesium chloride into the skin rather than evaporating.

For the exemplary compositions provided herein, the monohydric aliphatic alcohol and the polyol in combination comprise about 30% to about 99.9% by weight of the composition. In other exemplary compositions, the monohydric aliphatic alcohol and the polyol in combination comprise about 60% to about 99% by weight of the composition. Further representative ranges for the weight percent for the combination of the aliphatic alcohol and the polyol are about 30-40%, about 40-50%, about 50-60%, about 60-70%, about 70-80%, about 80-85%, about 5-90%, about 90-95%, about 95-98%, about 95-99%, about 0-75%, and about 50-90%.

Exemplary compositions as provided herein will generally comprise a greater percent by weight of the monohydric aliphatic alcohol in comparison to the polyol. For example, advantageous compositions as described herein may comprise from about 50% (w/w) to about 95% (w/w) monohydric aliphatic alcohol, from about 5% (w/w) to about 40% (w/w) polyol, and from about 0.1% (w/w) to about 10% (w/w) magnesium salt. Some preferred compositions as described herein may comprise from about 60% (w/w) to about 90% (w/w) monohydric aliphatic alcohol, from about 5% (w/w) to about 35% (w/w) polyol, and from about 0.2% (w/w) to about 5% (w/w) magnesium salt.

Illustrative liquid compositions may contain, for example, any one or more of the following weight-weight percentages of monohydric aliphatic alcohol, including ranges between each of the following values: 50%, 55%, 60%, 65%, 70%, 75%, 80%, 85%, 90% or 95% alcohol, where preferably, the weight percent alcohol is greater than the weight percent polyol. Further representative ranges for the alcohol component, which may be combined with w/w amounts or ranges for the magnesium salt and other formulation components as provided herein are from: 50-55% w/w, 50-60% w/w, 50-65% w/w, 50-70% w/w, 50-75% w/w, 50-80% w/w, 50-85% w/w, 50-90% w/w, 50-55% w/w, 55-60% w/w, 55-65% w/w, 55-70% w/w, 55-75% w/w, 55-80% w/w, 55-85% w/w, 55-90% w/w, 55-95% w/w, 60-65% w/w, 60-70% w/w, 60-75% w/w, 60-80% w/w, 60-85% w/w; 60-90% w/w, 60-95% w/w, 65-70% w/w, 65-75% w/w, 65-80% w/w, 65-85% w/w; 65-90% w/w, 65-95% w/w, 70-75% w/w, 70-80% w/w, 70-85% w/w, 70-90% w/w, 70-95% w/w, 75-80% w/w, 75-85% w/w, 75-90% w/w, 75-95% w/w, 80-85% w/w, 80-95% w/w, 80-95% w/w, 85-90% w/w, 85-95% w/w, 90-95% w/w.

Representative amounts of a polyol component, include, any one or more of the following: 5%, 10%, 15%, 20%, 25% 30%, 35% or 40% (w/w), including ranges between each of the foregoing, such as, for example: 5%-10% w/w, 5-15% w/w, 5-20% w/w, 5-30% w/w, 5-35% w/w, 5-40% w/w, 10-15% w/w, 10-20% w/w, 10-25% w/w, 10-30% w/w, 10-35% w/w, 10-40% w/w, 15-20% w/w, 15-25% w/w, 15-30% w/w, 15-35% w/w, 15-40% w/w, 20-25% w/w, 20-30% w/w, 20-35% w/w, 20-40% w/w; 25-30% w/w, 25-35% w/w, 25-40% w/w, 30-35% w/w, 30-40% w/w, or 35-40% w/w.

Generally, the ratio between the monohydric aliphatic alcohol and the polyol is in a range of 1:1 to 99:1 by weight. As set forth above, the composition will generally comprise a greater percent by weight of the monohydric aliphatic alcohol in comparison to the polyol. Exemplary w/w ratios of alcohol to polyol include, for example, about 1:1, 1.5:1, 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, and 95:1. The composition may comprise a w/w ratio between the monohydric aliphatic alcohol and the polyol between about 1:1 to 20:1, or from about 1:1 to about 15:1, or from about 1:1 to about 10:1, or from about 2:1 to about 20:1, or from about 2:1 to about 10:1, or from about 2:1 to about 7:1.

In one embodiment, the greater percent by weight of the monohydric aliphatic alcohol in comparison to the polyol provides a composition that transitions from a wet, liquid composition to a dry formulation when applied to the skin in less than about 3 minutes, less than about 2.5 minutes, less than about 2 minutes, less than about 1.5 minutes, or less than about 1 minute. The monohydric aliphatic alcohol is, in one embodiment, one that evaporates when applied to the skin, where the surface temperature is between about 33.5-36.9° C., in less than about 3 minutes, less than about 2.5 minutes, less than about 2 minutes, less than about 1.5 minutes or less than about 1 minute. Evaporation of the monohydric aliphatic alcohol leaves on the skin surface a residual composition comprised of the polyol and the magnesium salt dissolved in the polyol, along with any other composition ingredients that are non-volatile at skin surface temperature.

The instant compositions may also contain relatively small amounts, e.g., less than about 10% (w/w) of one or more auxiliary excipients suitable for topical use including but not limited to pH modifying agents, preservatives, thickening agents, gel-forming agents, emulsifying agents, antioxidants, scent agents, and the like. Compounds suitable for incorporation may be found, e.g., in R. C. Rowe, et al., *Handbook of Pharmaceutical Excipients* (4$^{th}$ Ed.), Pharmaceutical Press, London, 2003.

Gelling agents which may be used in the topical compositions include conventional gelling agents well known for their gelling properties, such as, for example, cellulose ethers such as hydroxypropyl cellulose, hydroxypropyl methylcellulose, carboxymethyl cellulose, sodium carboxymethyl cellulose, hydroxyethyl cellulose, and the like; vinyl alcohols; vinyl pyrrolidones; natural gums such as karaya gum, locust bean gum, guar gum, gelan gum, xanthan gum, gum arabic, tragacanth gum, carrageenan, pectin, agar, alginic acid, sodium alginate and the like, and methacrylates such as those available under the tradename Eudragit® from Rohm Pharma. Other gelling agents include polyoxyethylene-polyoxypropylene copolymers (poloxamers) such as those available under the tradename "Lutrol®", and the like. Preferred gelling agents are those absent free carboxyl groups such as, for instance, hydroxypropylcellulose, hydroxypropylmethylcellulose, hydroxyethylcellulose, methylcellulose, organo/cold water soluble cellulose, hydroxyethylmethylcellulose, ethylcellulose, ethyl(hydroxyethyl)cellulose. For substituted celluloses, a moderate to high degree of substitution is preferred in order to increase the solubility of the gelling agent in a selected solvent system. The preferred degree of substitution is at least 1.0, or preferably in the range of 1.2 to 6.0, or more preferably in the range of 2.5 to 4.5.

The composition may also contain an antioxidant. The amount of antioxidant, if present, will typically range from about 0.005% to about 3.0% by weight of the composition. Illustrative ranges include from about 0.01% to about 2.5% by weight antioxidant, from about 0.05% to about 2% by weight antioxidant, and from about 0.1% to about 1.5% by weight anti-oxidant. Illustrative amounts of antioxidant include 0.01%, 0.025%, 0.05%, 0.075%, 0.1%, 0.2%, 0.3%, 0.4%, 0.5%, 0.6%, 0.7%, 0.8%, 0.9% and 1% by weight. In one embodiment, the amount of antioxidant comprised within the composition is 0.01% by weight. In another embodiment, the amount of antioxidant comprised within the formulation is 0.2% by weight. Suitable antioxidants include, for example, butylated hydroxyanisole (BHA), butylated hydroxytoluene (BHT), tertiary butyl hydroquinone, propyl gallate, α-tocopherol, sodium metabisulfite, and the like. One preferred class of antioxidants are sulfur-containing antioxidants such as sodium metabisulfite, glutathione, N-acetylcysteine, thioproline, and taurine. Additional preferred compositions comprise an antioxidant selected from the list consisting of a sulfite compound, BHT, sodium selenite, DL-alpha tocopherol, a combination of dithioerythreitol and DL-alpha tocopherol, and sodium erythorbate. Sulfurous acid salts and organic esters (referred to collectively as "sulfites") are also preferred, such as bisulfites, pyrosulfites, metabisulfites, and sulfites.

In one or more embodiments, the topical composition comprises a suitable amount (e.g., about 0.005% to about 3.0% by weight) of a sulfite compound, e.g., a sulfite, metabisulfite or bisulfite salt, where the sulfite is accompanied by a suitable counterion.

The composition may further contain one or more preservatives in an amount typically ranging from about 0.01% to about 2.0% by weight of the composition. Illustrative preservatives include, for example, phenoxyethanol, methyl paraben, propyl paraben, butyl paraben, benzyl alcohol, and the like.

The topical composition may also comprise a small amount, such as 0.1% to 10% by weight, of one or more compounds effective to introduce a favorable scent or aroma, such as a natural oil or other suitable agent. Suitable essential oils include, for example, plant essential oils from eucalyptus, frankincense, patchouli, peppermint, lemon, lavender, orange, rosehip, rosemary, tea tree, jasmine, and the like. For example, in one or more embodiments, the composition comprises a small amount, such as 0.1% to 5% by weight, of 1,8-cineole, or some other essential oil.

The combination of polyol and 1,8-cineole can be particularly effective in preventing the skin from scaling and extreme dryness, especially when administration is for an extended period of time, e.g., for 2 weeks or more. Signs of dry skin which can be prevented include both scaling and itching.

The topical composition may be in a number of different forms, including, for example, a solution, liquid, spray, foam, lotion, gel and the like. Preferably, the composition is a liquid, adheres to the skin, and has a smooth feel. Generally, preferred compositions are absent nanoparticles and/or microparticles, although in some instances, the composition may comprise nanoparticles and/or microparticles. For additional information regarding suitable formulations, see, for example, "Remington: The Science and Practice of Pharmacology," 22nd edition, (Pharmaceutical Press, 2013).

A wide variety of methods may be used for preparing the compositions described herein. Broadly speaking, the compositions may be prepared by combining together the components of the compositions, as described herein, at a temperature and for a time sufficient to provide a pharmaceutically effective and desirable composition. The term "combining together", as used herein, means that all of the components of the compositions are combined and mixed together at about the same time, or that various components are combined in one or more sequences or orders of addition to provide the desired product. The composition can be prepared on a weight/weight (w/w) or a weight/volume (w/v) basis. The composition will generally be readily spreadable, e.g., on a surface of the skin, and preferably will not be runny.

The composition may be prepared by, e.g., admixture of the ingredients typically through the use of vigorous agitation such as high shear mixing. Mixing can also be accomplished by any suitable method using any suitable manual or automated means. Optional additional steps include those which result in the addition of one or more of the optional auxiliary ingredients as set forth above. Methods for preparing a pharmaceutical formulation are well known in the art and are described, for example, in Handbook of Pharmaceutical Formulations: Liquid Products, Vol 3, S. Niazi., CRC Press, 2004.

The composition may be topically applied directly to the affected areas of the skin, for example, using the fingertips, a sponge applicator, a cotton applicator, by spraying, aerosolization, or any other suitable method. The compositions provided herein are useful for treating any condition that is susceptible to treatment with a magnesium salt. The compositions provided herein may be used, for example, for treating conditions such as acne, impetigo, cellulitis, erysipelas, folliculitis, furuncles, carbuncles, Lyme disease and other skin infections, rosacea, seborrheic dermatitis, bullous dermatoses, cutaneous sarcoidosis, Kaposi's sarcoma, and neutrophilic dermatoses, and inflammation associated therewith. Types of acne include, for example, acne vulgaris, acne rosacea, acne conglobata, acne fulminans, gram-negative folliculitis, and pyoderma faciale, among others. For example, the composition may be used for treating moderate to severe acne, and the acne may be nodular or cystic.

In one or more embodiments, the method comprises the step of administering a topical composition as provided herein to an accessible body surface of a human or an animal in need of such treatment. Generally, the composition is applied in a conventional amount from once to several times weekly or daily on the affected areas of the skin, until the acne or condition being treated has visibly diminished or disappeared. For example, the topical composition may be applied topically at least once daily for a period of at least 1 month, or may be applied to the skin once or twice daily for a period of from 6 to 52 weeks or even longer. The number of applications and course of treatment will vary with the severity of the condition being treated, patient considerations, and the like. Thus, the composition may, in certain instances by applied one daily, twice daily, once every other day, from one to three times weekly, from 1 to 4 times weekly, every 3 days, etc.

A conventional amount is an amount that is sufficient to spread, e.g., thinly spread, over the affected area. If desired, the efficacy of treatment may be quantified by using a grading system such as the Leeds system (O'Brien. S C., et al., *J. Dermatol Treat* 1998; 9:215-220), the Comprehensive Acne Severity Scale (Tan, J K, et al., *J. Cutan Med Surg* 2007 November; 11(4211-6), or the Global Acne Grading System (Doshi, A., et al., *Int. J. Dermatol* 1997 June 36(6); 416-8). In one or more embodiments, the efficacy of treatment is assessed by a visual examination of the affected area. In some cases, prophylactic treatment may be continued even if the condition has visibly diminished or disappeared, as a preventative measure. In some embodiments, the efficacy of treatment is assessed by an evaluation of a reduction in total lesion count, where application of a topical composition as described herein is effective to result in a reduction in total lesion count as measured from the commencement of treatment.

Turning now to consideration of the Examples, various exemplary embodiments of the topical compositions are described. Example 1 describes the preparation of ten exemplary compositions, identified in Table 1 by composition numbers 1-10. Magnesium chloride (anhydrous) was used in the compositions in an amount between 0.3 wt % to 4.6 wt %. The solvent system was comprised of ethanol and propylene glycol. The ratio of ethanol to propylene glycol ranged from 2.0 (composition #10) to 3.9 (composition #1, 2, 3, and 7). Other than composition #8, the compositions were thickened using between about 0.2-0.6 wt % of a thickening agent. Sodium metabisulfite was included at 0.2 wt % in all of the exemplary compositions other than composition #7. The essential oil cineole was included at between 1-5 wt % in several of the compositions.

An in vivo study of an exemplary topical composition was conducted using minipigs, as described in Example 2. The test animals were randomized into a 7-day treatment group and a 20-day treatment group. An exemplary formulation, identified in Table 2 of Example 2 and referred to as MG06, was prepared. The MG06 formulation was comprised of, inter alia, 0.6 wt % magnesium chloride (anhydrous), 77.6% ethanol, and 20.0 wt % (propylene glycol ethanol/propylene glycol ratio of 3.9). The formulation was applied topically to the animals each day until the end of the 6 day (Group 1) or 20 day (Group 2) test period. The dosing site on each animal was inspected daily for erythema or edema. The absence of erythema and edema from the dosing site in both the test groups demonstrate that the compositions are non-irritating to the skin. Accordingly, in one embodiment, a method for treatment is contemplated, where a composition comprised of a magnesium salt in an anhydrous solvent system of a monohydric alcohol and a polyol is applied to the skin, the composition lacking a pharmaceutically or therapeutically active ingredient (other than the magnesium salt). The composition when applied to a local application site on the skin at least once daily for a period of 6 days, 7 days, 10 days or 20 days does not cause irritation as evidenced by lack of erythema and edema at the local application site.

Examples 3 and 4 describe further studies using a composition comprising a magnesium salt in a solvent system comprising ethanol and propylene glycol (e.g., from 50-99.9 w/w %). The water content for the composition, as measured by Karl Fischer titration, was less than 5%, less than 2%, less than 1.0%, and less than 0.5%. The specific composition used in the studies was identified as MG06-2. The MG06-2 formulation was comprised of, inter alia, 0.6 wt % magnesium chloride (anhydrous), 77.6% ethanol, and 20.0 wt % propylene glycol (ethanol/propylene glycol ratio of 3.9; Table 4 in Example 3). In Example 3, the formulation was applied to a shaved skin area on rats. The application site was inspected at defined intervals for up to 24 hours after application to evaluate the skin for erythema, redness, irritation, and/or edema using a modified Draize score. The study results demonstrated that the composition when applied to a local application site on the skin does not cause irritation as evidenced by lack of erythema and edema at the local application site. In Example 4, using an in vitro eye irritation model the eye irritation effects of MG06-2 were evaluated. This evaluation provided a cell viability target for compositions, where in one embodiment, cell viability measured using a methylthiazoly diphenyl tetrazolium bromide (MTT) assay is greater than 60% after exposure to the composition relative to the initial value for MTT cell viability when tested with the MATTEK EPIOCULAR model according to the MATTEK EPIOCULAR Eye Irritation Test Protocol.

Example 5 describes a study in human patients where the topical composition identified as MG06-2 was evaluated for the treatment of acne. The subjects had moderate to severe inflammatory, non-nodular acne vulgaris. Each subject was treated with the topical composition by applying to the area affected by acne an amount of the composition each day for a period of 12 weeks. At regular two-week intervals the subjects were evaluated by an investigator and the acne lesions were scored. In the treated population, a reduction of 11.3 inflammatory lesions was observed at the 12-week time point relative to baseline. Also, using the Investigator's Global Assessment (IGA), the proportion of subjects in the population with at least a two-grade reduction in IGA to clear ("0") or almost clear ("1") was 17.1%. Accordingly, the compositions described herein are effective in the treatment of certain dermatological skin conditions and in the reducing of symptoms associated with dermatological diseases or conditions, such as non-nodular acne vulgaris. In one embodiment, the composition is effective to provide at least a two grade reducing in acne severity based on the IGA scale in at least 10%, 15%, or 20% of the subjects by daily treatment for 12 weeks.

Example 6 describes a study in four human patients where the topical composition identified as MG06-2 was evaluated for the treatment of rosacea. The subjects had moderate rosacea. Each subject was treated with the topical composition by applying to the area affected by acne an amount of the composition each day for a period of 4 weeks. At regular two-week intervals the subjects were evaluated by an investigator and the rosacea lesions were scored. In the treated population, a reduction of 13.3 lesions was observed at the 4-week time point relative to baseline. This represented a 60% reduction in lesion count at the 4-week time point relative to baseline. Also, using the Investigator's Global Assessment (IGA), the proportion of subjects in the population with at least a two-grade reduction in IGA to clear ("0") or almost clear ("1") was 75%. Accordingly, the compositions described herein are effective in the treatment of certain dermatological skin conditions and in the reducing of symptoms associated with dermatological diseases or conditions, such as rosacea. In one embodiment, the composition is effective to provide at least a two-grade reducing in acne severity based on the IGA scale in at least about 10%, 15%, 20%, or 50% of the subjects by daily treatment for 4 or 12 weeks.

Additional advantages and features of the instant compositions are described throughout the instant document.

Thus, several advantageous properties are associated with the compositions and topical treatment methods described herein. The topical compositions are effective to deliver a magnesium salt (e.g. magnesium chloride) to the skin. Moreover, the compositions described herein are easy to apply, not sticky, and do not occlude the skin. The compositions are effective for treatment of acne. The compositions demonstrate no or minimal irritation potential.

EXAMPLES

The following examples are put forth to provide those of ordinary skill in the art with a complete disclosure and description of how the composition, its components, active ingredients, solvents, and the like, are prepared and evaluated, along with related methods, and are intended to be purely exemplary. Thus, the examples are in no way intended to limit the scope of what the inventors regard as their invention. There are numerous variations and combinations, e. g., component concentrations, desired solvents, solvent mixtures, antioxidants, and other mixture parameters and conditions that may be employed to optimize composition characteristics such as purity, yield, stability, odor, color, viscosity, penetration, and the like. Such are considered as well within the scope of the present disclosure.

Example 1

Topical Compositions

Table 1 provides additional illustrative topical compositions. The compositions are prepared by mixing the various components as previously described. Each column lists the percentage by weight of the component listed at the left side of each row in the composition. Each column adds to a total of 100%.

TABLE 1

EXEMPLARY COMPOSITIONS

| | EXEMPLARY COMPOSITION # | | | | | | | | | |
|---|---|---|---|---|---|---|---|---|---|---|
| | 1 | 2 | 3 | 4 | 5 | 6 | 7 | 8 | 9 | 10 |
| Magnesium source | | | | | | | | | | |
| Magnesium chloride anhydrous | 0.3 | 0.6 | 1.2 | 2.3 | 4.6 | 1.2 | 1.2 | 4.6 | 4.6 | 4.6 |
| Monohydric aliphatic alcohol | | | | | | | | | | |
| Ethanol | 78.9 | 78.6 | 78.0 | 71.9 | 64.6 | 77.0 | 77.2 | 65.2 | 65.0 | 60.0 |
| Polyol | | | | | | | | | | |
| Propylene glycol | 20 | 20 | 20 | 25 | 30 | 20 | 20 | 30 | 30 | 30 |
| Other components | | | | | | | | | | |
| Sodium metabisulfite | 0.2 | 0.2 | 0.2 | 0.2 | 0.2 | 0.2 | — | 0.2 | 0.2 | 0.2 |
| Hydroxypropyl cellulose HF (HPC HF) | 0.6 | 0.6 | 0.6 | 0.6 | 0.6 | 0.6 | 0.6 | — | 0.2 | 0.2 |
| Cineole | — | — | — | — | — | 1 | 1 | — | — | 5 |

Example 2

In Vivo Minipig 7- and 20-Day Repeat Dose Patch Study

A minipig topical application study was conducted over a period of either 7 days or 20 days to evaluate the dermal toxicity associated with repeat dose applications of the test article shown in Table 2. The study was performed using four non naïve, antibiotic free female minipigs, weighing between 20 and 30 kg and of 12-18 months age.

TABLE 2

MG06 FORMULATION

|  | % (w/w) |
|---|---|
| Hydroxypropyl cellulose (KLUCEL ® HF) | 0.6% |
| Magnesium Chloride, anhydrous | 0.6% |
| Ethanol, anhydrous | 77.59% |
| Propylene Glycol | 20.0% |
| Eucalyptol | 1.0% |
| Sodium Metabisulfite | 0.2% |
| Quinoline Yellow | 0.01% |

On Day 0, the animals were weighed and anesthetized. The right and left flank area were carefully clipped and shaved, and application sites of 3 cm×3 cm each or approximately about 10 $cm^2$ were marked. Test articles were applied topically using a positive displacement pipette and spreading in the marked test area using metal spatula in the amounts described in Table 3. Dosing continued daily until Day 6 (Group 1) and Day 20 (Group 2). Animals 151 and 152 were in Group 1. Animals 251 and 252 were in Group 2. Prior to daily dosing, treatment sites were gently wiped once with soap followed by a gentle wash with phosphate buffer saline (PBS). Body weights were measured once weekly.

TABLE 3

SUMMARY OF DOSING SITES TREATMENT

| | Animals 151/251 | | | Animals 152/252 | | |
|---|---|---|---|---|---|---|
| Dosing Site | Test Article | Dose/ Formu- lation | Volume (µL) | Test Article | Dose/ Formu- lation | Volume (µL) |
| L1 | MG06 | 0.6% mag- nesium chloride | 25 | MG06 | 0.6% mag- nesium chloride | 125 |

Dosing sites was evaluated daily for erythema and edema using a modified Draize scoring system. Photographs were taken prior to dose administration on Day 0 and daily thereafter. Skin pigmentation was visually noted daily. Additionally, UV lamp photos of the dosing sites were taken on Day 0 and at the end of the dosing (Day 7 for Group 1 and Day 20 for Group 2). At the end of the study, animals were sacrificed and skin tissues were collected from the dosing sites, along with one untreated site.

No abnormal weight changes were observed. No skin irritation was noted throughout the treatment period as indicated by a lack of erythema and edema.

Example 3

In Vivo Rat Single Dose Study Skin Irritation and Histology

A skin irritation study was conducted in rats using a composition comprised of a magnesium salt in a solvent system comprising ethanol and propylene glycol. The composition is set forth in Table 4.

TABLE 4

Composition of Topical Formulation MG06-2

| Ingredient | wt % |
|---|---|
| Hydroxypropyl cellulose | 0.6% |
| Magnesium chloride (anhydrous) | 0.6% |
| Ethanol (anhydrous) | 77.59% |
| Propylene Glycol | 20.0% |
| 1,8-Cineole | 1.0% |
| Sodium meta-bisulfite | 0.2% |
| D&C Yellow #10 | 0.01% |
| Measured pH for composition | 4.86 |
| Measured water content for composition | 0.39% |

The day before treatment, a 15 $cm^2$ area was shaved on the dorsal area in the region of the shoulders and back of each of six male Sprague-Dawley rats and a 10 $cm^2$ area was marked as the application test site. The rats were randomly divided evenly into 2 groups, a treatment group and a no-treatment group. Each rat in the treatment group received application of 2.5 mg/$cm^2$ of the composition listed in Table 4 (MG06-2). The composition was applied uniformly to the application test site on each rat at time T=0. No topical was applied to the rats in the no-treatment group.

Skin irritation was evaluated using the modified Draize scoring system. Evaluations were performed prior to and immediately after application and at the following time points: 30 minutes, 1 hour, 3 hours, 6 hours, and 24 hours after application. No measurable erythema, redness, irritation, and/or edema were observed. The modified Draize score was 0 for each of the time points and each of the rats in the study. This indicates that each of the compositions tested was non-irritating.

No abnormal weight changes were observed in any treatment group.

The rats were euthanized shortly after the 24-hour time point. Biopsies were taken from the skin of the rats and frozen or fixed in 10% formalin to allow further histological analysis, including staining with hematoxylin and eosin. No significant changes were observed in any of the skin sections when the treatment group was compared to those in the no treatment group.

Example 4

In Vitro Eye Irritation Test in Epiocular EIT Model

The eye irritation effects for one composition comprising a magnesium salt in a solvent system comprising ethanol and propylene glycol was evaluated. This was compared to positive and negative controls, described below.

The United Nations publishes the "Globally Harmonized System of Classification and Labelling of Chemicals (GHS)" for classification of eye effects (Globally Harmonized System of Classification and Labelling of Chemicals (GHS); Chapter 3: Serious Eye Damage/Irritation—Second Revised Edition, United Nations; No. ST/SG/AC. 10/30, Rev 2, 2007). Tested chemicals and compositions are classified into one of 3 categories: no eye damage (i.e., GHS category "No Category"), irreversible eye damage (i.e., GHS category 1), or reversible eye irritation (i.e., GHS category 2).

In this study, the eye irritation effects were evaluated by following the procedure described in the MATTEK EPI-OCULAR Eye Irritation Test (EIT) Protocol (EpiOcular™ Eye Irritation (OCL-200-EIT) for the Prediction of Acute Ocular Irritation of Chemicals, Reference No. MK-24-007-0055, MatTek Corporation, Ashland, Mass.). The MATTEK EPIOCULAR model is a commercially available 3-dimensional model of the human corneal epithelium derived from normal human epidermal keratinocytes. The endpoint of the test is an estimation of cell viability by MTT assay (methylthiazolyldiphenyltetrazolium bromide). Since the region of the eye that is most commonly damaged by a composition would be the outer surface of the cornea and this model emulates the outer portion of the cornea, this model is commonly used to evaluate the eye irritation potential for chemicals. The use of the EPIOCULAR EIT protocol is specified in OECD Test Guideline No. 492. This test thus provided an indication of the level of eye irritation or damage that would be observed in an in vivo test.

Compositions were classified as having no eye damage (i.e., GHS category "Not Classified") if the MTT cell viability was greater than 60% relative to control samples of ultrapure water. Ethyl acetate was used as a positive control and ultrapure water was used as a negative control. Cell viability was measured via optical density as measured by a MULTISKAN SPECTRUM plate reader (Thermo Fisher Scientific Oy, Vantaa, Finland). MTT cell viability for MATTEK EPIOCULAR models were tested following an exposure to a composition (or a control) in a humidified incubator maintained at 37° C. in a 5% $CO_2$ atmosphere for 30 minutes. The cell viability scale was measured relative to the post-exposure cell viability for the negative control (ultrapure water). The mean cell viability for the negative control was used to set the value that corresponded to 100% cell viability. The composition was classified as having eye irritation or damage (i.e., GHS category 1 or 2) if the post-exposure cell viability was less than or equal to 60% of the corresponding mean cell viability for the negative control sample. The composition MG06-2 as described in Table 4 of Example 3 was assessed.

The results of the study showed that the mean post-exposure MTT cell viability relative to the negative control was 48% for composition MG06-2. Thus, it was determined that compositions MG06-2 was eye irritating or damaging (UN GHS category 1 or 2).

Thus, some compositions according to the invention have a MTT cell viability after exposure to the composition relative to the initial value for MTT cell viability of greater than 60% when tested with the MATTEK EPIOCULAR model according to the MATTEK EPIOCULAR EIT Protocol.

Example 5

Method of Treating Acne

A clinical trial was conducted with composition MG06-2 of Example 3 (Table 4). The multi-center trial evaluated the composition in 74 subjects, aged 9 to 40, with moderate-to-severe inflammatory, non-nodular acne vulgaris. Subjects applied composition MG06-2 to their faces daily for a continuous period of 12 weeks. Subjects visited investigating sites at baseline, 2 weeks, 4 weeks, 8 weeks, and 12 weeks. At each visit, investigators observed the subjects and asked subjects about any adverse events that they had experienced since their last visit.

The results of the study were that in the intent-to-treat (ITT) population, a reduction of 11.3 inflammatory lesions was observed at the 12-week time point relative to baseline.

The trial also measured reduction in Investigator's Global Assessment (IGA). The proportion of subjects in the ITT population with at least a two-grade reduction in IGA to clear ("0") or almost clear ("1") was 17.1%.

No treatment related serious adverse events were reported in the clinical trial.

These trial results demonstrate that the compositions described herein, particularly MG06-2, are effective in the treatment of certain dermatological skin conditions, such as non-nodular acne vulgaris.

Example 6

Method of Treating Rosacea

A clinical trial was conducted with composition MG06-2 of Example 3 (Table 4). The single-center trial evaluated the composition in four subjects with moderate rosacea. Subjects applied composition MG06-2 to their faces daily for a continuous period of four weeks. Subjects visited investigating site at baseline and four weeks. At each visit, investigators observed the subjects and asked subjects about any adverse events that they had experienced since their last visit.

The results of the study were that a reduction of 13.3 inflammatory lesions was observed at the 4-week time point relative to baseline, reducing from an average of 25.3 lesions to an average of 8.8 lesions. This represented a 60% reduction in lesion count at the 4-week time point relative to baseline.

The trial also measured reduction in Investigator's Global Assessment (IGA). The proportion of subjects in the ITT population with at least a two-grade reduction in IGA to clear ("0") or almost clear ("1") was 75%.

No treatment related serious adverse events were reported in the clinical trial.

These trial results demonstrate that the compositions described herein, particularly MG06-2, are effective in the treatment of certain dermatological skin conditions, such as rosacea.

The invention claimed is:

1. A topical composition, comprising:
   a magnesium salt dissolved in an anhydrous solvent comprised of a monohydric aliphatic alcohol and a polyol, wherein the composition does not comprise an active pharmaceutical ingredient other than the magnesium salt, wherein the monohydric aliphatic alcohol and polyol comprise 50-99.9% of the weight of the composition, and wherein the monohydric aliphatic alcohol and the polyol are in a ratio of from about 1:1 to 99:1.

2. The composition of claim 1, wherein the monohydric aliphatic alcohol is present in the composition at a greater percent by weight than the polyol.

3. The composition of claim 1, wherein the monohydric aliphatic alcohol to polyol ratio is between about 2:1 to 10:1.

4. The composition of claim 1, wherein the monohydric aliphatic alcohol is selected from the group consisting of ethanol, isopropanol, propyl alcohol, tert-butyl alcohol, and combinations thereof.

5. The composition of claim 1, wherein the monohydric aliphatic alcohol is a liquid at room temperature, the polyol is a liquid at room temperature, or both the monohydric aliphatic alcohol and the polyol are liquids at room temperature.

6. The composition of claim 1, wherein the polyol is a C3-C8 diol or triol.

7. The composition of claim 1, wherein the polyol is propylene glycol.

8. The composition of claim 1, wherein the magnesium salt is selected from the group consisting of magnesium chloride, magnesium sulfate, magnesium salicylate, and combinations thereof.

9. The composition of claim 1, wherein the magnesium salt is selected from the group consisting of the anhydrous magnesium chloride, anhydrous magnesium sulfate, anhydrous magnesium salicylate, and combinations thereof.

10. The composition of claim 1, comprising between about 0.1% to about 10% by weight magnesium salt.

11. The composition of claim 10, wherein the magnesium salt is magnesium chloride.

12. The composition of claim 1, further comprising a thickening agent.

13. The composition of claim 12, wherein the thickening agent is hydroxypropyl cellulose.

14. The composition of claim 1, wherein the composition does not comprise an antibiotic.

15. A method for treating a dermatological condition or disease, comprising:
topically applying to an exterior epithelial surface of a human body a composition according to claim 1 at least once daily for a period of at least one week.

16. A method for treating acne or rosacea in a human subject, comprising topically applying to a local skin region affected by acne or rosacea a composition according to claim 1 at least once daily for a period of at least one week.

17. The method of claim 16, wherein the acne or rosacea of the human subject is reduced from moderate or severe to clear or almost clear, according to the Investigator's Global Assessment (IGA), following 12 weeks of daily application of the composition.

18. The method of claim 16, wherein an acne lesion count or rosacea lesion count for the human subject is reduced by more than 10 lesions following 12 weeks of daily application of the composition.

19. A method for manufacturing the composition of claim 1, comprising: combining the magnesium salt, the monohydric aliphatic alcohol, and the polyol to form a mixture, and agitating the mixture to form a solution in which the magnesium salt is dissolved.

* * * * *